United States Patent [19]  [11] 4,029,799
Cartés et al.  [45] June 14, 1977

[54] CERTAIN ANALGESICALLY ACTIVE SUBSTITUTED BENZYL PYRIDINE COMPOUNDS

[75] Inventors: Juan Bosch Cartés; Jorge Canals Cabiro; Ricardo Granados Jarque, all of Barcelona; Cristobal Martinez Roldán; Fernando Rabadan Peinado, both of Madrid, all of Spain

[73] Assignee: Laboratorios Made, S.A., Spain

[22] Filed: Apr. 29, 1975

[21] Appl. No.: 572,864

[30] Foreign Application Priority Data

Feb. 20, 1975 Spain .................................. 434904

[52] U.S. Cl. ............................ 424/263; 260/295 R; 260/297 R
[51] Int. Cl.² ................. C07D 213/30; A61K 31/44
[58] Field of Search .................. 260/295 R, 297 R; 424/263

[56] References Cited

OTHER PUBLICATIONS

Clarke, J.A.C.S., vol. 31, (1909), pp. 585–589.
Carey et al., J. Chem. Soc., (1933), pp. 346–347.
Wagner et al., Synthetic Organic Chem., 195, p. 484.

Primary Examiner—Henry R. Jiles
Assistant Examiner—Bernard Dentz
Attorney, Agent, or Firm—Marn & Jangarathis

[57] ABSTRACT

2-(3,4,5-Trimethoxy benzyl)-3,4-dimethyl pyridine and 2-(3,4,5-trimethoxyphenyl)-(3,4-dimethyl-2-pyridyl)-ethoxy-methane and their pharmaceutically acceptable acid addition salts have analgesic properties.

3 Claims, No Drawings

CERTAIN ANALGESICALLY ACTIVE SUBSTITUTED BENZYL PYRIDINE COMPOUNDS

The present invention relates to the preparation of 2-(3,4,5-trimethoxybenzyl)-3,4-dimethylpyridine of formula

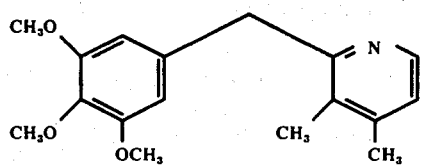

from 3,4,5-trimethoxyphenyl-(3,4-dimethyl-2-pyridyl)-carbinol of formula II, and of two collateral products of the preparation, namely 3,4,5-trimethyoxyphenyl-(3,4-dimethyl-2-pyridyl)-ethoxymethane of formula III, and the acetate of 3,4,5-trimethoxyphenyl-(3,4-dimethyl-2-pyridyl)-carbinol of formula IV

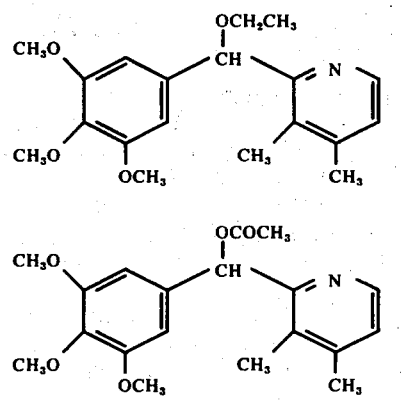

The above-mentioned compounds (with the exception of that of formula II, are novel substances with possible pharmacological interest as analgesiscs.

The process is carried out by adding thionyl chloride on a solution of the carbinol II in anhydrous benzene, keeping the temperature below 20° C, as a result of which the intermediate product 3,4,5-trimethoxyphenyl-(3,4-dimethyl-2-pyridyl)-methyl chloride is obtained, which is reduced with zinc powder and hydrochloric acid. After being made alkaline, the resulting mixture is extracted with ether and concentrated, to give 2-(3,4,5-trimethoxybenzyl)-3,4-dimethylpyridine (I) in solid form which is recrystallized from ether.

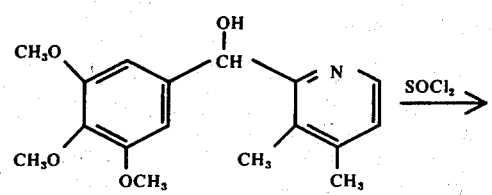

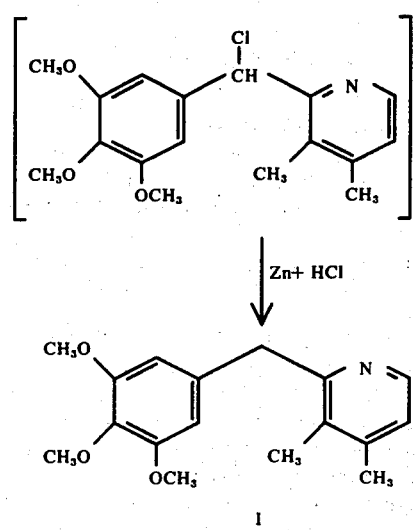

Furthermore, the reduction of the chloride intermediate, as obtained above, with zinc and glacial acetic acid leads, after being made alkaline and extraction with an organic solvent, to impure benzylpyridine I containing the acetate of 3,4,5-trimethyoxyphenyl-(3,4-dimethyl-2-pyridyl)-carbinol (IV), as a result of the reaction between acetic acid and the intermediate 3,4,5-trimethyoxyphenyl-(3,4-dimethyl-2-pyridyl)-methyl chloride.

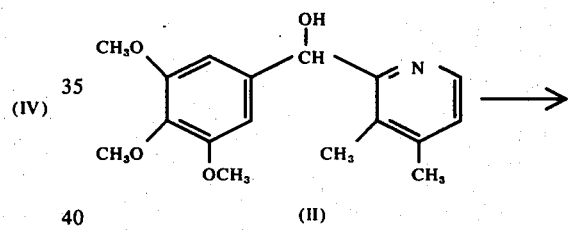

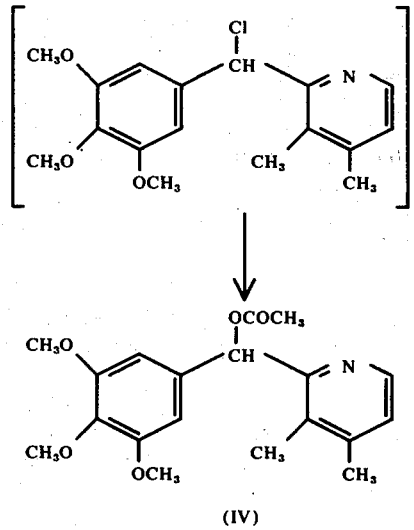

Finally, treatment of the above chloride in absolute ethanol yields 3,4,5-trimethoxyphenyl-(3,4-dimethyl-2-pyridyl)-ethoxymethane (III) in the form of its hydrochloride, a compound which is purified by recrystallization from acetone.

The following examples are given only for illustration, and in no event should they be regarded as limitative of the scope of the invention.

EXAMPLE 1

Production of 2-(3,4,5-trimethoxybenzyl)-3,4-dimethyl-pyridine (I)

41.4 g of 3,4,5-trimethoxyphenyl-(3,4-dimethyl-2-pyridyl)-carbinol (II) are dissolved in 180 ml of anhydrous benzene and 10.8 ml of thionyl chloride dissolved in 30 ml of anhydrous benzene are added, keeping the temperature below 20° C. The mixture is agitated for 3 hours at ambient temperature, and is made alkaline with a 25% aqueous solution of sodium hydroxide. The organic layer is dried and evaporated, giving 38.8 g of a reddish residue which is dissolved in 300 ml of 2N hydrochloric acid. 30 g of powdered zinc are slowly added to this solution, and the mixture is heated under reflux with agitation for 7 hours, at the end of which it is allowed to cool, there then being added a 20% solution of sodium hydroxide to produce a strongly basic pH. It is extracted several times with ether. The ether extracts, after having been dried over anhydrous sodium sulphate, are evaporated to dryness yielding 18 g (Yield 50%) of a solid which, recrystallized from ether, has a melting points of 105°–107° C.

Analysis calculation for $C_{17}H_{21}NO_3$: C, 71.05; H, 7.35; N, 4.87. Found: C, 70.96; H, 7.50; N, 4.81.

EXAMPLE 2

Production of 3,4,5-trimethoxyphenyl-(3,4-dimethyl-2-pyridyl)-ethoxymethane (III).

6.9 g of 3,4,5-trimethoxyphenyl-(3,4-dimethyl-2-pyridyl)-carbinol (II) are dissolved in 30 ml of anhydrous benzene and 1.8 ml of thionyl chloride dissolved in 10 ml of anhydrous benzene are added, keeping the temperature below 20° C. The mixture is agitated for 2 hours at ambient temperature and is made alkaline with a 25% aqueous solution of sodium hydroxide. The organic layer is dried and evaporated, yielding 6.6 g of a reddish residue which is heated under reflux for 6 hours in the presence of 250 ml of absolute ethanol. The resulting residue, on evaporation of the solvent, is digested with anhydrous acetone, and a white precipitate appears which is recrystallized from anhydrous acetone-ether. Thus are obtained 3.4 g (Yield 40%) of 3,4,5-trimethoxyphenyl-(3,4-dimethyl-2-pyridyl)-ethoxymethane hydrochloride, m.p.188°–191° C.

Analysis calculation for $C_{19}H_{25}NO_4HCl$: C, 62.04; H, 7.07; N, 3.81; Cl, 9.66; Found: C, 62.06; H, 7.33; N, 3.67; Cl, 9.86.

EXAMPLE 3

Production of the acetate of 3,4,5-trimethoxyphenyl-(3,4-dimethyl-2-pyridyl)-carbinol (IV)

5 g of 3,4,5-trimethoxyphenyl-(3,4-dimethyl-2-pyridyl)-carbinol (II) are dissolved in 25 ml of anhydrous benzene and 1.3 ml of thionyl chloride dissolved i 5 ml of benzene are added, keeping the temperature below 20° C. The mixture is agitated for 2 hours at ambient temperature and is made all aline with a 25% aqueous solution of sodium hydroxide. The organic layer is dried and evaporated, yielding 5.4 g of a reddish residue which is heated under reflux for 15 hours in the presence of 150 ml of glacial acetic acid. The acetic acid is removed by distillation under vacuum, and the resulting residue is made alkaline with 25% sodium hydroxide and is extracted with ether. The organic layer is dried, evaporated to dryness, and is purified by distillation, as a result of which there is obtained an oil which crystallizes on dissolving it in ether (3.7 g, Yield 65%(, this being identified as the acetate of 3,4,5-trimethoxyphenyl-(3,4-dimethyl-2-pyridyl)-carbinol (IV). An analysis sample exhibits a m.p. of 108°–111° C (acetone-ether).

Analysis calculated for $C_{19}H_{23}NO_5$: C, 66.07; H, 6.71; N, 4.06. Found: C, 66.18; H, 6.88; N, 3.94.

PHARMACOLOGICAL SECTION

PRODUCT 1. 2-(3,4,5-trimethoxybenzyl)-3,4-dimethylpyridine (I).

Dextropropoxyphene was taken as the comparison product.

A. ACUTE TOXICITY

Acute toxicity studies were carried out in I.C.R. Swiss mice weighing 24 ± 2 g, of both sexes. The products were administered intraperitoneally (i.p.). Acute toxicity was calculated by the method of Lichfield and Wilcoxon. The results are given in Table A.

TABLE A

| Products | Lethal dose 50 ($LD_{50}$) |
|---|---|
| 2-(3,4,5-trimethoxybenzyl)-3,4-dimethylpyridine (I) | 250 mg/kg |
| Dextropropoxyphene | 140 mg/kg |

B. ANALGESIC ACTIVITY

The analgesic activity of 2-(3,4,5-trimethoxybenzyl)-3,4-dimethylpyridine compound (I) was investigated in female albino I.C.R. Swiss mice weighing 24 ± 2 g. For this the Hot Plate Test was used at 55° C. 4 groups of mice each comprising 10 animals, were assembled. The distribution of the groups was according to the following scheme:-

Group 1 — Control - 0.2 ml of distilled $H_2O$
Group 2 — Compound I-0.2 ml of a solution of 2-(3,4,5-trimethoxybenzyl)-3,4-dimethylpyridine (I), 3 mg/ml.
Group 3 — Compound I-0.2 ml of a solution of 2-(3,4,5-trimethoxybenzyl)-3,4-dimethylpyridine (I), 6 mg/ml.
Group 4 — Dextropropoxyphene - 0.2 ml of a solution of dextropropoxyphene, 6 mg/ml.

The products were injected intraperitoneally, and the measurements of analgesia were made 30 minutes after the administration of the drugs. Note was taken of the time taken for an animal to jump off the hot plate. The results are shown in Table B.

TABLE B

| Product | Dose | Jump-off time in seconds* | Significance |
|---|---|---|---|
| Control | — | 77 ± 9.272 | — |
| Compound I | 25 mg/kg | 77 ± 8.203 | N.S. |
| Compound I | 50 mg/kg | 133.5 ± 12.581 | $p < 0.02$ |
| D-propoxyphene | 50 mg/kg | 102.4 ± 10.302 | $p < 0.05$ |

*Average values ± standard mean error.

It may be observed that for equal doses, 2-(3,4,5-trimethoxybenzyl)-3,4-dimethylpyridine (I) is more analgesic than d-propoxyphene, and since it is also less toxic, the therapeutic index of 2-(3,4,5,-trimethoxybenzyl)-3,4-dimethyl-pyridine (I) is greater than that of dextropropoxyphene.

We claim:

1. A compound selected from the group consisting of 2-(3,4,5-trimethoxybenzyl)-3,4-dimethylpyridine, 3,4,5-trimethoxyphenyl-(3,4-dimethyl-2-pyridyl)-ethoxymethane and pharmaceutically acceptable acid addition salts thereof.

2. A pharmaceutical composition exhibiting analgesic properties which comprises an analgesically effective amount of a compound selected from the group consisting of 2-(3,4,5-trimethoxybenzyl)-3,4-dimethylpyridine, 3,4,5-trmiethoxyphenyl-(3,4-dimethyl-2pyridyl)-ethoxymethane and pharmaceutically acceptable acid addition salts thereof and a pharmaceutically acceptable carrier therefor.

3. A process for treating an animal comprising: administering to the animal an analgesically effective amount of a compound selected from the group consisting of 2-(3,4,5-trimethoxybenzyl)-3,4-dimethylpyridine, 3,4,5-trimethoxyphenyl (3,4-dimethyl-2-pyridyl)-ethoxymethane and pharmaceutically acceptable acid addition salts thereof.

* * * * *

UNITED STATES PATENT OFFICE
CERTIFICATE OF CORRECTION

Patent No. 4,029,799                    Dated 6/14/77

Inventor(s) Juan Bosch Cartes et al

It is certified that error appears in the above-identified patent and that said Letters Patent are hereby corrected as shown below:

Col. 3, line 25, delete "4,87" and substitute --4.87--;
       line 59, delete "i" and substitute --in--;
       line 61, delete "all aline" and insert --alkaline--.
Col. 4, line 4, delete " ( " after "65%" and insert -- ) --.
Col. 5, line 11, delete "3,4,5-trmiethoxyphenyl" and substitute --3,4,5-trimethoxyphenyl--. (Claim 2)
Col. 6, line 8, insert -- - -- after "trimethoxyphenyl". (Claim 3)

Signed and Sealed this

Twenty-eighth Day of March 1978

[SEAL]

Attest:

RUTH C. MASON
Attesting Officer

LUTRELLE F. PARKER
Acting Commissioner of Patents and Trademarks